US008628461B2

(12) United States Patent
Mohl (10) Patent No.: US 8,628,461 B2
(45) Date of Patent: Jan. 14, 2014

(54) METHOD AND DEVICE FOR THE INTERMITTENT OCCLUSION OF A BLOOD VESSEL

(75) Inventor: Werner Mohl, Altenmarkt-Thennenberg (AT)

(73) Assignee: Miracor Medical Systems GmbH, Vienna (AT)

( * ) Notice: Subject to any disclaimer, the term of this patent is extended or adjusted under 35 U.S.C. 154(b) by 898 days.

(21) Appl. No.: 12/317,474

(22) Filed: Dec. 22, 2008

(65) Prior Publication Data

US 2010/0130810 A1    May 27, 2010

(30) Foreign Application Priority Data

Nov. 27, 2008 (AT) ................. A 1856/2008

(51) Int. Cl.
*A61N 1/362* (2006.01)
(52) U.S. Cl.
USPC ............................................. 600/17; 623/2.1
(58) Field of Classification Search
USPC ............................................. 600/17; 623/2.1
See application file for complete search history.

(56) References Cited

U.S. PATENT DOCUMENTS

| 3,707,960 | A | * | 1/1973 | Freed | 600/381 |
| 4,459,977 | A | * | 7/1984 | Pizon et al. | 600/17 |
| 4,934,996 | A | * | 6/1990 | Mohl et al. | 600/17 |
| 4,969,470 | A | * | 11/1990 | Mohl et al. | 600/486 |
| 6,210,318 | B1 | * | 4/2001 | Lederman | 600/18 |
| 2004/0172004 | A1 | * | 9/2004 | Mohl | 604/509 |

OTHER PUBLICATIONS

Mohl, Werner et al. "Coronary Sinus Library, ICSO and PICSO" Society of Coronary Sinus Interventions, 2003. A. Holzhausens Nfg., Austria.
Mohl et al., "Intermittent pressure elevation of the coronary venous system as a method to protect ischemic myocardium," *Interact CardioVac Thorac Surg.*, 2005, 4:66-69.
Syeda et al., "The salvage potential of coronary sinus interventions: Meta-analysis and pathophysiologic consequences," *J Thorac Cardiovasc Surg.*, 2004, 124:1703-1712.

* cited by examiner

*Primary Examiner* — Niketa Patel
*Assistant Examiner* — Mallika D Fairchild
(74) *Attorney, Agent, or Firm* — Fish & Richardson P.C.

(57) ABSTRACT

A device for the intermittent occlusion of a blood vessel, in particular a vein draining the organ system, comprising an occlusion device which is activatable for intermittent occlusion and positionable in the blood vessel, at least one sensor for the continuous or periodical detection of at least one physiological measurement, and a control device to which the at least one physiological measurement is fed and which cooperates with the occlusion device to control the intermittent occlusion of the blood vessel as a function of said measurement.

7 Claims, 6 Drawing Sheets

METHOD AND DEVICE FOR THE INTERMITTENT OCCLUSION OF A BLOOD VESSEL

Priority is claimed to Austria Pat. App. No. A 1856/2008, filed Nov. 27, 2008, hereby incorporated by reference in its entirety. The invention relates to an implantable device for the intermittent occlusion of a blood vessel, in particular a vein draining the organ system.

The invention further relates to a method for treating the heart and circulatory disturbances as well as a device for carrying out this method.

Arterial blood, which supplies the heart muscle, is able to pass through healthy heart tissue while nourishing the same, yet has difficulty reaching ischemic tissue. As a result, the supply of ischemic tissue with nutrients and the discharge of metabolic catabolites from such ischemic tissue will be impaired. In this context, it has already been proposed to supply ischemic tissue with blood through retrograde perfusion. The retrograde perfusion of blood in coronary veins, in particular, plays an important role in the field of myocardial protection during a surgery at the open heart. A typical such intervention comprises, for instance, the balloon dilatation of an arteriosclerotically constricted coronary artery. That method, which is also known as percutaneous transluminal coronary angioplasty (PTCA), comprises the introduction of a balloon catheter into the region of the coronary artery stenosis under X-ray control and the compression of the osclerotic plaque by the inflation of the balloon, which is located on the end of the catheter. During the dilatation of the balloon, no supply of the tissue with oxygen-containing blood takes place downstream in the artery with functional changes in the ischemic area of the myocard being detectable already at dilatations lasting longer than 30 seconds. Consequential problems of the ischemic protection of the myocard will also arise at other interventions for coronary vascularization such as, e.g., atherectomy, coronary endoprostheses and laser applications. An undersupply of a myocardial area will also exist at an acute myocardial infarction.

In the context of a short-time ischemic protection, the retro-infusion of arterial blood or other nutritive fluids into a vein of the ischemic myocardial area concerned has been performed for some time. In doing so, the blood is pumped into the nutritive capillaries of the ischemic area via the respective vein, thus supplying the myocardium with oxygen and substrates in that region.

A device for the retroinfusion of coronary veins, by which a pressure-controlled, intermittent coronary sinus occlusion can be performed, has become known from U.S. Pat. No. 4,934,996. That device comprises a means for occluding the sinus such as, e.g., an inflatable balloon catheter, a pressure measuring unit for measuring the fluid pressure within the coronary sinus, and a control unit which generates triggering signals for the occlusion means to trigger or release an occlusion. The control unit is devised such that the pressure maximum in the coronary sinus will be measured during each heartbeat, a plateau value of the pressure maxima of consecutive heartbeats is estimated by calculation, and the occlusion of the coronary sinus is released based on the plateau value of the pressure maxima.

The occlusion of the coronary sinus causes a pressure increase and, as a result, a retroperfusion of blood via the respective vein into the nutritive capillaries of the ischemic area so as to enable the supply of nutrients to that area. At a release of the occlusion, the retroperfused blood is flushed out, with the metabolic waste products being carried off at the same time. In the method according to U.S. Pat. No. 4,934,996, a systolic pressure curve is, thus, estimated based on the measurement of the pressure maximum in the coronary sinus during each heartbeat, the intermittent occlusion being controlled as a function of the plateau value of the systolic pressure curve. The course of the estimated systolic pressure curve also allows for a conclusion as to the performance of the heart, wherein, for instance, the slope of the curve will reflect the contractility of the heart. The slope of the curve naturally also influences the height of the plateau value, a lower plateau value being reached with a flatter curve, wherein, compared to a healthy heart, said plateau, after all, is reached after an extended time period upon induction of the occlusion. A shift in the curve will also result if a coronary vessel, during an interventional action like PTCA or stenting, is occluded either temporarily or, due to a complication, even for a longer period of time such that the pressure curve will rise more slowly and take more time to reach the plateau.

Methods for intermittently occluding a blood vessel and, in particular, the coronary sinus have also become known from WO 03/008018 A2, WO 2005/120602 A1 and WO 2005/120601 A1. Such methods are applicable even with acute myocardial infarctions, wherein it has been demonstrated that a reduction of the area of infarction is feasible by the periodic occlusion of the venous run-off.

It has also been already proposed to divert blood into poorly supplied vessel zones from the coronary veins of areas that are well supplied with blood.

The hitherto known devices are exclusively suitable for the temporary treatment of a patient during a surgical intervention. Such an intervention, as a rule, involves considerable expenditures and will require a physician not only for the placement of the occlusion device in the blood vessel to be occluded. The operation of the occlusion device too will require permanent medical supervision. During the intermittent occlusion, critical parameters such as, for instance, the pressure in the occluded blood vessel have to be monitored, and physiological measurements have to be constantly analyzed as to whether the desired improvement of the condition and, in particular, an increase in the performance of the heart have actually occurred on account of the treatment. Furthermore, it has to be decided, based on the measurements, at what time the treatment, i.e. the intermittent occlusion procedure, can be terminated.

A disadvantage involved in the methods and devices for the intermittent occlusion of a blood vessel known from the prior art also resides in that, in most cases, treatment cannot be carried out before the patient has serious symptoms, i.e. at a time at which already irreversible damage has possibly already occurred. A preventive application of the intermittent occlusion of a blood vessel already at a minor deviation of specific physiological parameters from the desired patient-specific values is not possible as a rule.

The present invention aims to improve the methods and devices for the intermittent occlusion of a blood vessel known from the prior art to the effect that treatment expenditures will be reduced and no permanent medical supervision by a doctor will be required during the treatment.

The invention further aims to largely automate the control of the intermittent occlusion, said control having to be effected such that an optimum treatment result will be achieved.

To solve this object, the invention provides a device for the intermittent occlusion of a blood vessel, in particular a vein draining the organ system such as, e.g., the coronary sinus, which is implantable. In accordance with the invention, the device comprises an occlusion means which is activatable for intermittent occlusion and positionable in the blood vessel, at least one sensor for the continuous or periodical detection of at least one physiological measurement, a control device to which the at least one physiological measurement is fed and which cooperates with the occlusion means to control the intermittent occlusion as a function of said measurement, and an implantable anchoring means separate from the occlusion means and capable of being brought into operative connection with the blood vessel for positioning the occlusion means relative to the blood vessel.

The implantable device comprises all components required for an autonomous operation. In addition to the occlusion means, which is activatable for intermittent occlusion and positionable in the blood vessel, the implantable device comprises at least one sensor as well as a control device so as to enable the control of the occlusion means as a function of the measurements detected by the at least one sensor. The control may, for instance, comprise a pressure-dependent control as described in the documents U.S. Pat. No. 4,934,996, WO 03/008018 A2, WO 2005/120602 A1 and WO 2005/120601 A1. The control, in particular, comprises the determination of the optimum times at which the blood vessel is closed by the occlusion means, and those times at which the blood vessel is released again. The intermittent occlusion comprises a plurality of alternately performed occlusion and release phases. Furthermore, the device according to the invention comprises an anchoring means separate from the occlusion means, by the aid of which the occlusion means can be positioned within the blood vessel and relative to the same. By the aid of the anchoring means, a durable fixation of the occlusion means and, optionally, of the at least one sensor is feasible in a manner that the occlusion means can remain, and be completely automatically operated, within the blood vessel for a long time. The treatment of a patient will then only require a single surgical intervention by the physician, namely the implantation of the device according to the invention into a patient's blood vessel, said implantation encompassing not only the occlusion means but also the at least one sensor, the control means and the anchoring means. Following implantation, the patient may leave the hospital with the intermittent occlusion of the blood vessel being effected according to requirements. In this respect, it is conceivable that the initiation of the intermittent occlusion is triggered externally, for instance by the patient themselves or by a physician, or that automatic triggering takes place based on the measurements detected by the at least one sensor.

In the intermittent occlusion devices according to the prior art, the intermittent occlusion was performed by the aid of a balloon which was introduced into the blood vessel and expanded for the occlusion of the blood vessel and deflated for releasing the occlusion. The expansion and contraction of the balloon was effected by the aid of a gaseous or liquid medium which was pumped into the balloon and sucked off again. Such an occlusion means is not necessarily suitable for permanent implantation, since, on the one hand, an appropriate reservoir for the liquid or gaseous medium would have to be provided in the patient's body and, on the other hand, the risk of a burst of the balloon, and hence escape of the medium, would be too high. According to a preferred further development of the device according to the invention, the occlusion means is, therefore, not hydraulically or pneumatically operated, but configured as a mechanically or electrically driven occlusion means, with the drive being preferably activatable electrically. Such a mechanical or electrical drive for the occlusion means can be readily implanted, requiring just an electrical energy supply to be provided for the electrical activation of the drive. The electrical energy supply may be implanted in a patient's body on a suitable location in a manner similar to pacemakers, with the electrical connection lines to the occlusion means and to the drive of the occlusion means being conducted within the body. The electrical energy supply may, for instance, be integrated in the control device to form a single component part, thus reducing the expenditures involved in the surgical intervention.

Mechanically or electrically driven occlusion means are conceivable in a variety of configurations. According to a preferred configuration, the occlusion means may, for instance, comprise an electrically activatable valve. The occlusion means may preferably comprise an electrically activatable actuator formed, for instance, by an electromagnet. The actuator may cooperate with at least one component part which, as a function of the operation of the actuator or electromagnet, is movable between a position occluding the blood vessel and a position releasing the blood vessel. The actuator may, for instance, cooperate with a foldable membrane. According to another embodiment, the actuator may cooperate with a locking member to be deployed and closed like an umbrella.

A configuration in which the actuator is formed by a shape-memory material is also conceivable. The shape of such a material will, for instance, change as a function of the applied voltage or of the temperature. Even electroactive polymers can be used in this context.

In another configuration, at least one valve made, for instance, of conductive plastic can be provided, wherein the valve is able to push itself off a counter member, for instance a further valve, as a function of the respective electrical charge state, the valve thus being movable between a closing and opening position. Such mechanisms have, for instance, become known in the context of heart valves.

In configurations in which the occlusion means comprises at least one part which is movable between a closing position, in which the blood vessel is occluded, and an opening position, in which the blood vessel is not occluded, a preferred further development provides that the actuator, upon electrical activation, cooperates with the movable part to apply a force acting in the sense of closing. As a result, the movable part will be powered in the sense of closing and accordingly brought into the closing position against the resistance of the blood flow within the blood vessel so as to ensure the automatic reset of the movable part in the event of a possible failure of the actuator caused by the prevailing pressure of the congested blood, thus enabling the blood to subsequently flow through the blood vessel unimpeded. The operating safety of the device according to the invention will thereby be substantially enhanced.

In order to achieve a suitable anchorage of the occlusion means, the anchoring means is preferably designed as a vessel implant and, in particular, a radially expandable stent. Such stents are generally known in vascular surgery and, as a rule, designed such that they are introducible into the respective blood vessel in compressed form having a reduced outer diameter and, after having reached the desired position, can be brought into an expanded form having an enlarged outer diameter. In the expanded state, the stent will exert a controlled radial application pressure against the inner wall of the blood vessel so as to ensure the fixation of the assumed position. The holding force may be increased by a special structure of the stent jacket, e.g. a helix structure, or by friction-enhancing measures on the outer jacket.

At least part of the actuator may be received in the stent.

According to an alternative configuration, it is provided that the anchoring means is formed by an artificial vessel. The implantation of the device according to the invention in this case comprises the replacement of a portion of the blood vessel with the artificial vessel, which is connected with the adjoining region of the natural vessel so as to enable an anchorage of the occlusion means connected with the artificial vessel.

In a preferred manner, the configuration is further developed such that the anchoring means comprises or forms a reception space for the occlusion means. The occlusion means in this case is directly arranged in the anchoring means, e.g. in the stent or in the artificial vessel, thus offering the advantage of the implant being implantable as a prefabricated unit.

As already mentioned, the control of the occlusion means is performed as a function of at least one physiological measurement. In this context, the configuration is preferably further developed such that a timing element is provided to effect the detection of the at least one physiological measurement at predefined time intervals. The shorter the predefined time intervals, the more precise the control, since the respectively latest measurement will be taken as a basis for such control.

In a preferred manner, a memory for storing the physiological measurements and/or the occlusion procedures is provided, which is connected with a transmitter for the wireless transmission of the memory contents. In this case, an external evaluation instrument may, for instance, be provided to read out in a wireless manner the data contained in the memory and enable the patient and/or the attending physician to carry out a data analysis or evaluation. It will thus be feasible in a simple manner to check the function mode of the implantable device and provide regular diagnoses.

The control of the occlusion device may be performed in various ways. In a preferred manner, it is provided that the sensor is configured for the detection of a fluid pressure, fluid volume, flow, electrical resistance, electrical impedance, heart currents for establishing an electrocardiogram (ECG) and/or metabolic parameters such as, e.g., the $O_2$ saturation or pH or lactate content of the blood. In doing so, it is possible to measure either a single one or several of these parameters. Usually, the respective measurements must be fed to a computational or statistical evaluation in order to generate appropriate control signals for the occlusion means. The sensor may be arranged either within the blood vessel to be occluded, in particular on or near the occlusion means, or in a separate, yet likewise implantable unit outside the blood vessel, which harbours the power supply and/or the control device. Where several sensors are provided, at least one sensor can be arranged in the blood vessel and at least another sensor can be arranged in said separate unit.

The object underlying the present invention, according to a further aspect of the invention is achieved by a method for treating the heart or circulatory disturbances, comprising the intermittent occluding of a blood vessel, in particular a vein draining the organ system, wherein the blood vessel is alternately occluded and released. The method is characterized in that the quantity of at least one physiological value of the patient is determined at time intervals or continuously, the respective measurements are stored and a measurement series is obtained, that a computational and, in particular, statistical evaluation of the measurement series is performed, and that the intermittent occlusion is initiated or terminated as a function of the evaluation result.

To carry out this method, a device for the intermittent occlusion of a blood vessel, in particular a vein draining the organ system, is provided according to a further aspect of the invention, comprising
- an occlusion means activatable for intermittent occlusion,
- a control device connected with the occlusion means,
- at least one sensor for the continuous or periodical detection of at least one physiological measurement, and
- a measurement memory fed by the sensor and adapted to store a measurement series,
- wherein the measurement series is fed to the control device, which is configured for the computational and, in particular, statistical evaluation of the measurement series and cooperates with the occlusion means to initiate or terminate the intermittent occlusion as a function of the evaluation result.

The said method and device enable a fully automated operation, while, based on the computational and, in particular, statistical evaluation of the measurement series, allowing the determination of the optimum times at which the treatment by way of intermittent occlusion of the blood vessel can be initiated and terminated, respectively. Such an automated operation is, in particular, required where an occlusion means is permanently implanted in a blood vessel, since in those cases an action by the physician will no longer be possible as a rule. It is, therefore, necessary for the control device to decide, based on the detected measurements, whether and how long a treatment by the intermittent occlusion is to be performed. To this end, a computational and, in particular, statistical evaluation of the measurement series is provided according to the invention, wherein the procedure of the intermittent occlusion is initiated or terminated as a function of the evaluation result. As already mentioned, the procedure of the intermittent occlusion in this case comprises a sequence of alternating occlusion phases in which the blood vessel is occluded and release phases in which the blood vessel is released.

In order to enable as precise as possible a determination of the time of initiation or termination of the treatment, it is provided according to a preferred further development that the computational evaluation is performed after every measurement determination. The computational evaluation thus takes into account the latest measurement so as to effect a constant updating of the evaluation results.

The computational evaluation itself may be realized in various ways. According to a first preferred mode of procedure, it is provided that the computational evaluation of the measurement series comprises the conversion of the individual measurements of the measurement series to converted measurements so as to obtain a converted measurement series. A conversion will, for instance, be necessary if the physiological value to be used for evaluation cannot be directly measured. Measurable quantities in the context of the present invention preferably include the blood pressure in the region of the blood vessel, the blood mass or volume flow in the region of the blood vessel, the electrical resistance, the conductivity, the electrical impedance in the region of the blood vessel, in particular of the heart and/or lungs, the ECG and/or a metabolic parameter such as, e.g., the $O_2$ saturation and/or lactate content or pH of the blood.

According to a further preferred mode of operation, it is provided that the computational evaluation of the measurement series comprises the determination of the difference of the respectively last two measurements of the measurement series, or the difference of the respectively last two converted measurements of the derived measurement series, so as to obtain a series of difference values. The evaluation in this context may be realized in that the intermittent occlusion is initiated or terminated at the occurrence of a pregiven difference. Such jump behaviour of a measurement may indicate a critical state of the blood vessel or heart, thus calling for an immediate start of treatment. Sporadic jumps of measurements may, however, also be regarded as outliers due, for instance, to errors in the measurement detection. In order not to take any account of such outliers in the evaluation, the computational evaluation may preferably comprise a statistical evaluation by which the recognition of a trend is provided and short-term outliers are suppressed.

The computational evaluation of the measurement series may comprise a comparison of the individual measurements with a pregiven, absolute limit value in order to detect an inadmissible or critical state of the blood vessel or heart when said limit value is exceeded or fallen short of. Alternatively, a relative limit value may also be of interest, the configuration in this respect being preferably further developed such that the computational evaluation of the measurement series comprises the determination of the cumulated differences of the series of difference values. The cumulated difference reflects the difference between the last and first measurements of a measurement series.

According to a further preferred mode of operation, it is provided that the computational evaluation of the measurement series comprises the determination of the change in the measurements of the measurement series, or in the converted measurements of the converted measurement series, per time unit so as to obtain a derivative series. The change in the measurements per time unit reflects the speed of change and hence corresponds to the first derivative of the measurement curve over time.

A number of measurements will change with the heartbeat cycle, for instance the blood pressure, the volume or mass flow of the blood or the like, wherein, as a rule, merely the respective maximum or minimum value during a heartbeat will be of interest for evaluation. A further preferred further development, therefore, contemplates that the computational evaluation of the measurement series comprises the determination of local maxima and/or local minima of the values of the measurement series, the converted measurement series, the difference value series and/or the derivative series, and that a series of extreme values is formed from the local maxima or minima, respectively.

Moreover, it will frequently happen that a measurement, or the local maxima and/or local minima occurring during the respective heartbeats will rise or drop with each heartbeat during the occlusion phase. In this context, it may be advantageous to merely use for evaluation the maximum value occurring during an occlusions phase. Another preferred mode of operation, therefore, contemplates that the maximum or minimum of the mentioned values each occurring during an occlusion is selected as the local maximum or minimum, respectively.

The control device in which the computational evaluation of the measured values or measurement series is performed may cooperate with the occlusion device in various ways, the time of initiating or terminating the intermittent occlusion thus being determinable in various ways too. According to a preferred further development, it is provided in the context of the present invention that the computational evaluation of the measurement series comprises a comparison with a pregiven limit value, of the values of the measurement series, the converted measurement series, the difference value series, the derivative series and/or the extreme value series and/or the cumulated differences, with the intermittent occlusion being initiated upon achievement of the limit value. In the resting state, in which no intermittent occlusion is effected, it is thus monitored during the computational evaluation of the measurements, whether a pregiven limit value is reached. It is, for instance, possible to monitor the contractility of the heart by way of measurements. Furthermore, it is possible to diagnose an ischemia by way of characteristic changes in the ECG, e.g. by what is called an "ST elevation". If the contractility or the "ST elevation" reaches or falls below a limit value, which may be a patient-dependent predetermined value, the occlusion device is activated to perform an intermittent occlusion. The beginning of the intermittent occlusion may, for instance, also be determined by way of the $O_2$ saturation of the blood or by way of the pH and, in particular, the lactate content.

Another way of determining the optimum time of initiation of an intermittent occlusion resides in determining the electrical impedance of the thorax or of regions of the thorax like the lungs. The electrical impedance is indirectly proportional to the fluid content of the detected region such that, for instance, a left heart insufficiency causing a congestion of blood in the lungs may be detected by way of the electrical impedance. In this context, it is referred to WO 2008/070818 A2.

During the intermittent occlusion, the measurements are likewise evaluated as described, whereby the optimum time for terminating the intermittent occlusion must be determined. In this context, a preferred further development contemplates that the computational evaluation of the measurement series comprises the recognition or estimation of a plateau value of the values of the measurement series, the converted measurement series, the difference value series, the derivative series and/or the series of extreme values, whereby the intermittent occlusion is terminated at the plateau value or at a predetermined percentage of the plateau value. The achievement of a plateau value indicates that a characteristic measurement has changed and reached a stable final value. When reaching such a "steady state", the physiological parameters originally decreased to below a critical value or increased to above a critical value will again have attained a stable normal value such that the intermittent occlusion procedure can be terminated.

In a preferred further development, a new measurement series is each started at the initiation and/or termination of the intermittent occlusion such that the evaluation will only be based on the measurements respectively detected after the last initiation or termination of the intermittent occlusion.

The determined measurements, however, may not only be used to determine the initiation and termination of an intermittent occlusion, but may also be applied to control the individual occlusion and release phases during an intermittent occlusion.

In this context, it is preferably provided that the measurements determined during the occlusion of a blood vessel are each subjected to a separate computational evaluation, and that the individual occlusion phases of the intermittent occlusion are terminated as a function of the evaluation result. The same holds for the release phases, wherein it is preferably provided that the measurements determined during the release of a blood vessel are each subjected to a separate computational evaluation, and that the individual release phases of the intermittent occlusion are terminated as a function of the evaluation result.

In the following, the invention will be explained in more detail by way of exemplary embodiments schematically illustrated in the drawing. Therein.

Figure 1:
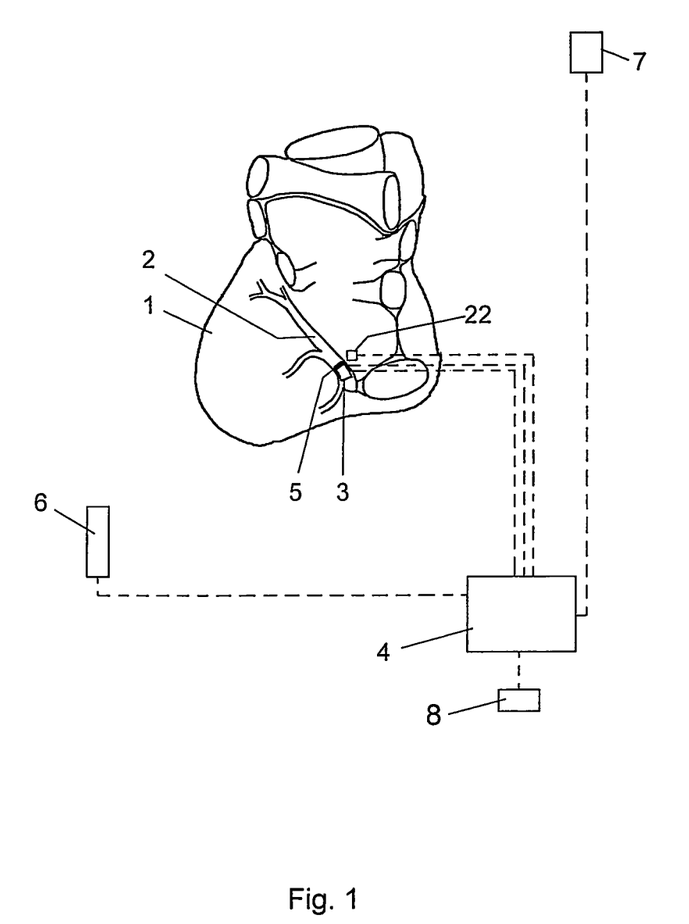
FIG. 1 depicts the implantable device according to the invention in the implanted state.

In FIG. 1, a human heart 1 is schematically illustrated. In the coronary sinus 2, an occlusion means 3 is arranged, which can be activated for the intermittent occlusion of the coronary sinus 2. The control device for activating the occlusion means is denoted by 4. The control device 4 is fed the measurements of a sensor 5 via a line. The sensor 5 is, for instance, designed as a blood pressure sensor, measuring the pressure in the coronary sinus. To the control device 4 is further connected an electrode 6 via which a current pulse can be emitted. By the aid of the sensor 7, which is arranged diametrically opposite the electrode 6 in respect to the heart 1 and the lungs (not illustrated), the electrical impedance of the thorax, or heart 1 and lungs, can be detected, which in turn allows for conclusions as to the contractility of the heart 1. Furthermore, a sensor 22 may be provided, which serves to measure the conductivity of the blood in the coronary sinus, wherein studies have revealed that the conductivity of the blood is a measure for the contractility of the heart. The measurements from sensors 5 and 7 are evaluated in the control device 4, with the occlusion means 3 being activated as a function of the evaluation result. In particular, the lengths of the individual occlusion and release phases are determined during the intermittent occlusion. Based on the measurements, the optimum times for the initiation and termination of the intermittent occlusion are, moreover, determined. The exact control algorithm will be explained by way of FIGS. 3 to 6.

The power supply of the control device 4 and optionally the occlusion means 3 is denoted by 8.

Figure 2:
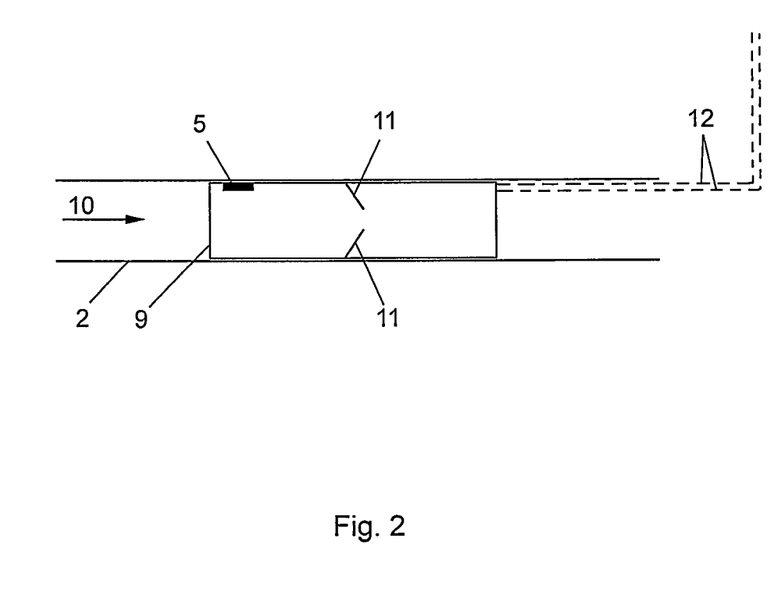
FIG. 2 is a cross-sectional view of an implantable occlusion device.

FIG. 2 details the coronary sinus, and it is apparent that an anchoring means 9 designed as a stent has been inserted into the coronary sinus 2. The stent 9 cooperates with the inner wall of the coronary sinus 2 to fix the stent 9 in its position. The blood flow direction with the opened occlusion means 3 is denoted by 10. The stent 9 carries a pressure sensor 5, which measures the pressure in the coronary sinus 2. The occlusion means is comprised of at least two valve-like component parts 11 which are movable between a closing position, in which the coronary sinus 2 is occluded, and an opening position, in which the coronary sinus is opened, i.e. not occluded. The movement of the valve-like component parts can be effected by pivoting. FIG. 2 depicts the valve-like component parts 11 in an intermediate position. For occlusion, the valve-like component parts 11 are pivoted into the closing position contrary to the sense of arrow 10 and held in that position by power load. As soon as the power load is stopped, i.e. the activation of the occlusion means is terminated, the valve-like component parts 11 are automatically pressed open by the prevailing blood pressure so as to cause the coronary sinus to open automatically. Such a configuration implicates that the coronary sinus 2 will also automatically open in the event of a possible malfunction caused, for instance, by an exhaustion of the power source, so that such malfunction will not cause damage to the organism.

When the occlusion means closes the coronary sinus 2 during an occlusion phase, the blood will congest in the coronary sinus 2 and retroperfuse into the surrounding tissue. When opening the occlusion means during the subsequent release phase, the congested blood will be washed out. The alternating occlusion and release phases are repeated until an improvement of the situation has been identified based on the measurements.

The stent 9 is connected with two electrical lines 12, one of which serves to transmit the measurements of the sensor 5 to the control device 4 and the other of which lines 12 serves to electrically activate the occlusion means.

Figure 3:
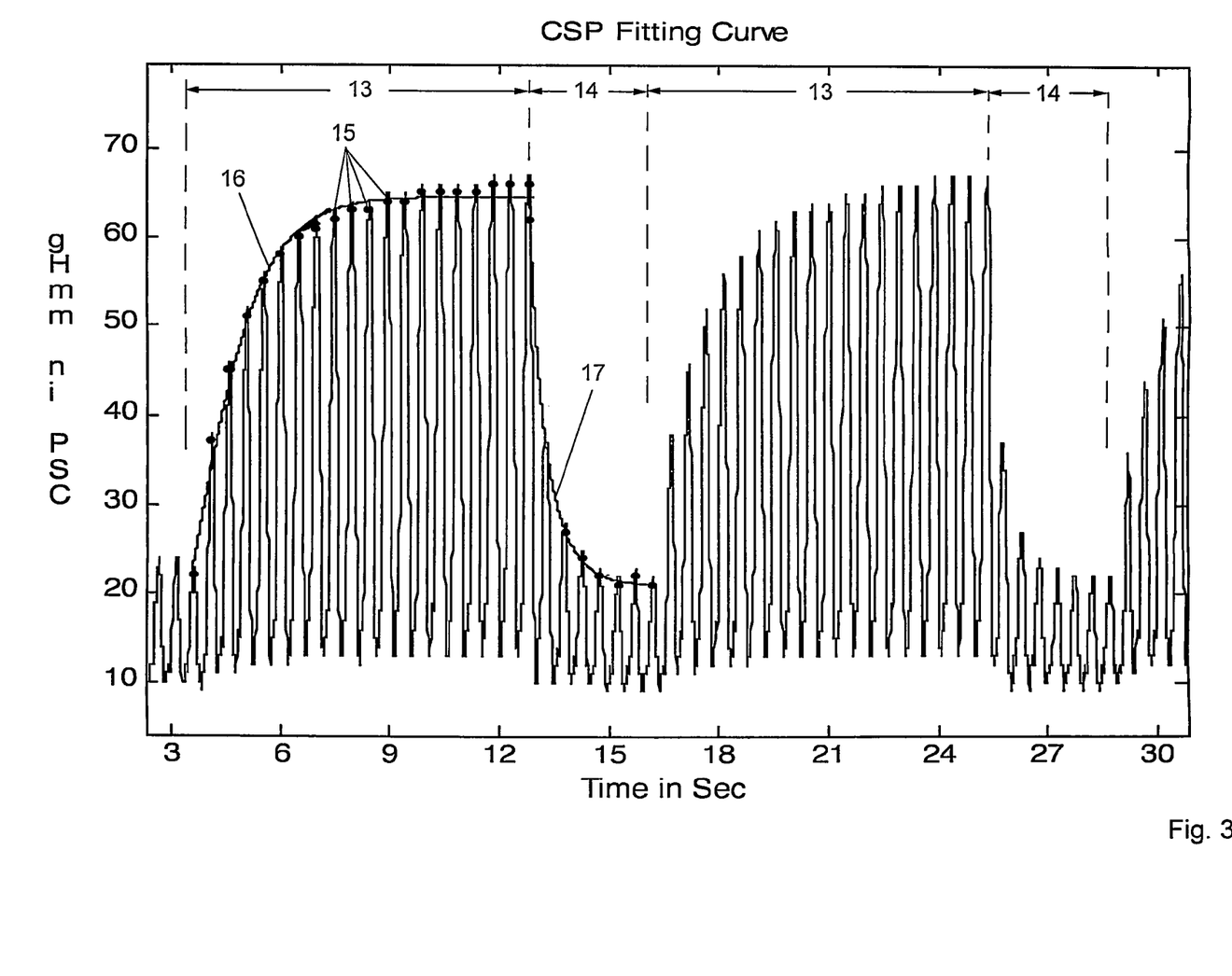
FIG. 3 represents a pressure curve provided by a pressure sensor.

FIG. 3 illustrates the measurements detected by the pressure sensor 5. The pressure curve indicates the pressure course in mmHg over time. It is apparent that the pressure maximum occurring at each heartbeat rises during the occlusion phase 13 with each heartbeat, until the pressure maxima have reached an upper plateau value, said pressure maxima being denoted by 15. During the release phase 14, the pressure will drop abruptly, thus causing the pressure maxima to reach a lower plateau value. The pressure maxima 15 form a series of extreme values. The pressure maxima 15 can be approximated by a curve 16 (occlusion phase) and a curve 17 (release phase). The approximation is preferably performed according to the method of least error squares. A selection of the time duration of the individual occlusion and release phases can be made based on the approximated curves 16, 17.

Figure 4:
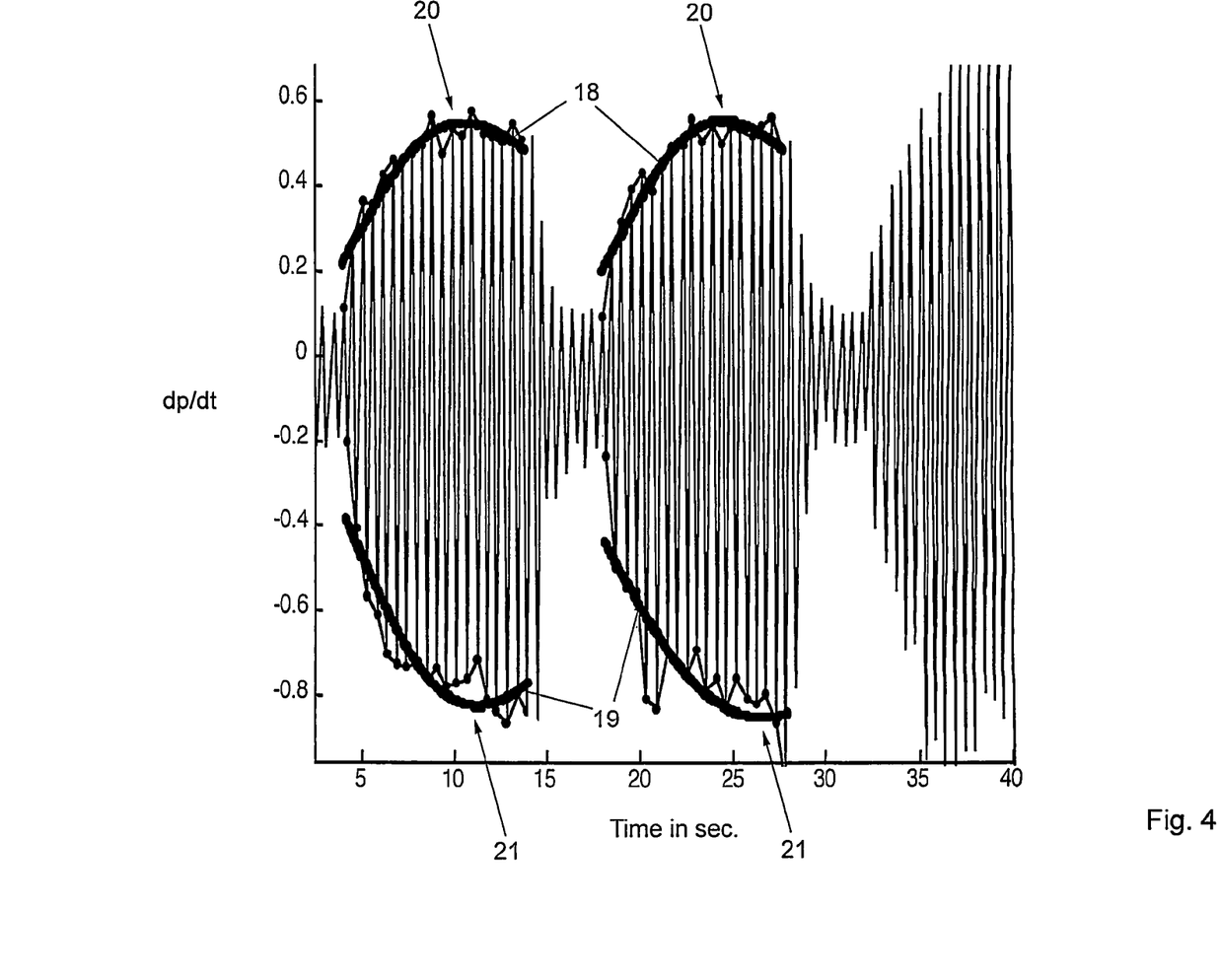
FIG. 4 shows the first derivative of the pressure curve.

The selection of the duration of the individual occlusion and release phases, however, can also be performed based on the time derivative dp/dt of the pressure curve. The first derivative dp/dt of the pressure curve is represented in FIG. 4. The curve indicates that a local maximum and a local minimum of the first derivative occur again during each heartbeat. The point of the local maximum indicates the time at which the pressure increase occurs fastest. The point of the local minimum indicates the time at which the pressure drop occurs fastest. FIG. 4 depicts the curve 18 approximated to the local maxima of the first derivative, and the curve 19 approximated to the local minima of the first derivative, for the occlusion phase. It is apparent that the maxima of the first derivative occurring at consecutive heartbeats at first rise until reaching the maximum at point 20 during the occlusion phase to decrease again afterwards. The same holds for point 21 of the minima of the first derivative occurring at consecutive heartbeats. Points 20 and 21 can be determined through calculation by zeroing the derivative of the approximated curves 18 and 19.

The positive values of the time derivative dp/dt of the pressure curve (cf. curve 18) serve as an indicator of the contractility of the heart, whereby the occlusion phase 13 is terminated when the contractility reaches a maximum. The contractility of the heart, however, may not only be determined by way of the time derivative dp/dt of the pressure curve, but instead based on the conductivity of the blood in the coronary sinus detected by the sensor 22.

Figure 5:
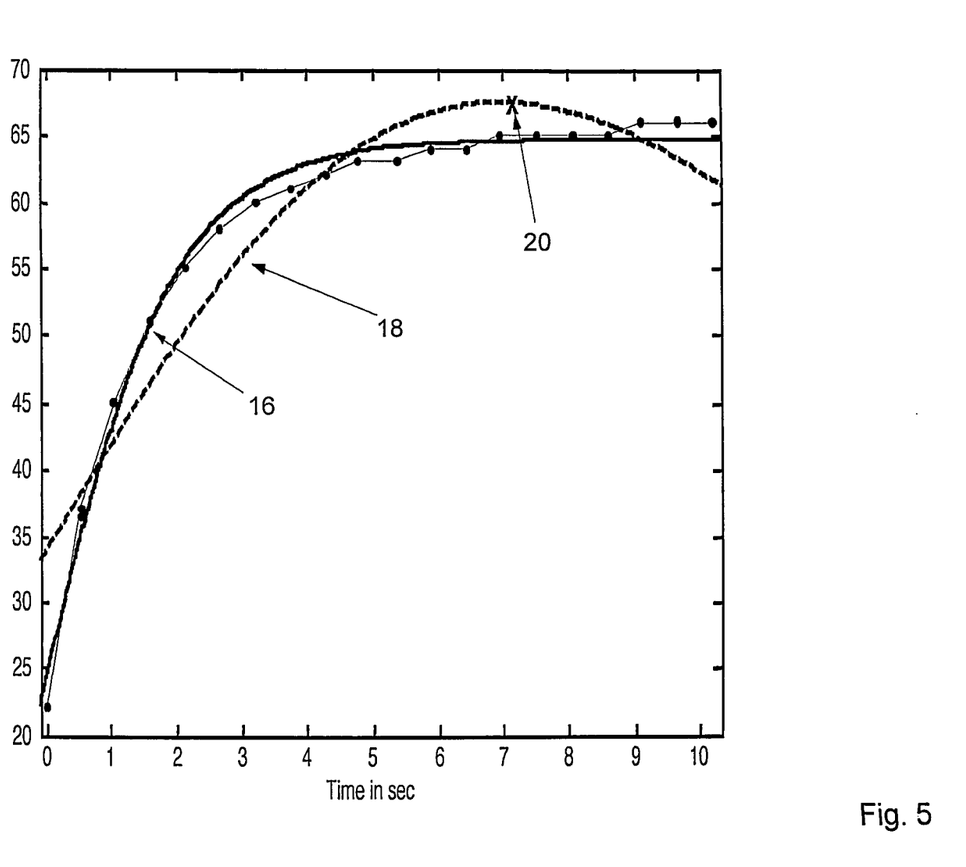
FIG. 5 shows the curves approximated to the local maxima of the pressure curve and the first derivative.

In the illustration according to FIG. 5, the curve 16 approximated to the local maxima of the pressure curve and the curve 18 approximated to the local maxima of the first derivative dp/dt of the pressure curve are represented. It is apparent that the maximum 20 of curve 18 offers a substantially better recognizable and more definite reference point for the termination of the occlusion phase than the plateau value of curve 16.

Even the negative values of the time derivative dp/dt can be used to determine the optimum time for terminating the respective occlusion phase. The negative values of the time derivative dp/dt serve as an indicator of the relaxation phase of the heart. The time of the maximum pressure drop speed (the time of the respective local minimum of the first derivative occurring during each heartbeat) actually constitutes the beginning of the isovolumetric relaxation phase of the heart. If the occlusion phase takes too long, the isovolumetric relaxation phase will be shortened. In order to avoid such shortening, the occlusion phase will have to be terminated in time. This will be achieved by the constant evaluation of the first derivative of the pressure curve in respect to the local minima, thus enabling, in combination with the determination of the heart currents (ECG), the calculation of the duration of the relaxation phase and the accomplishment of trend recognition.

Figure 6:
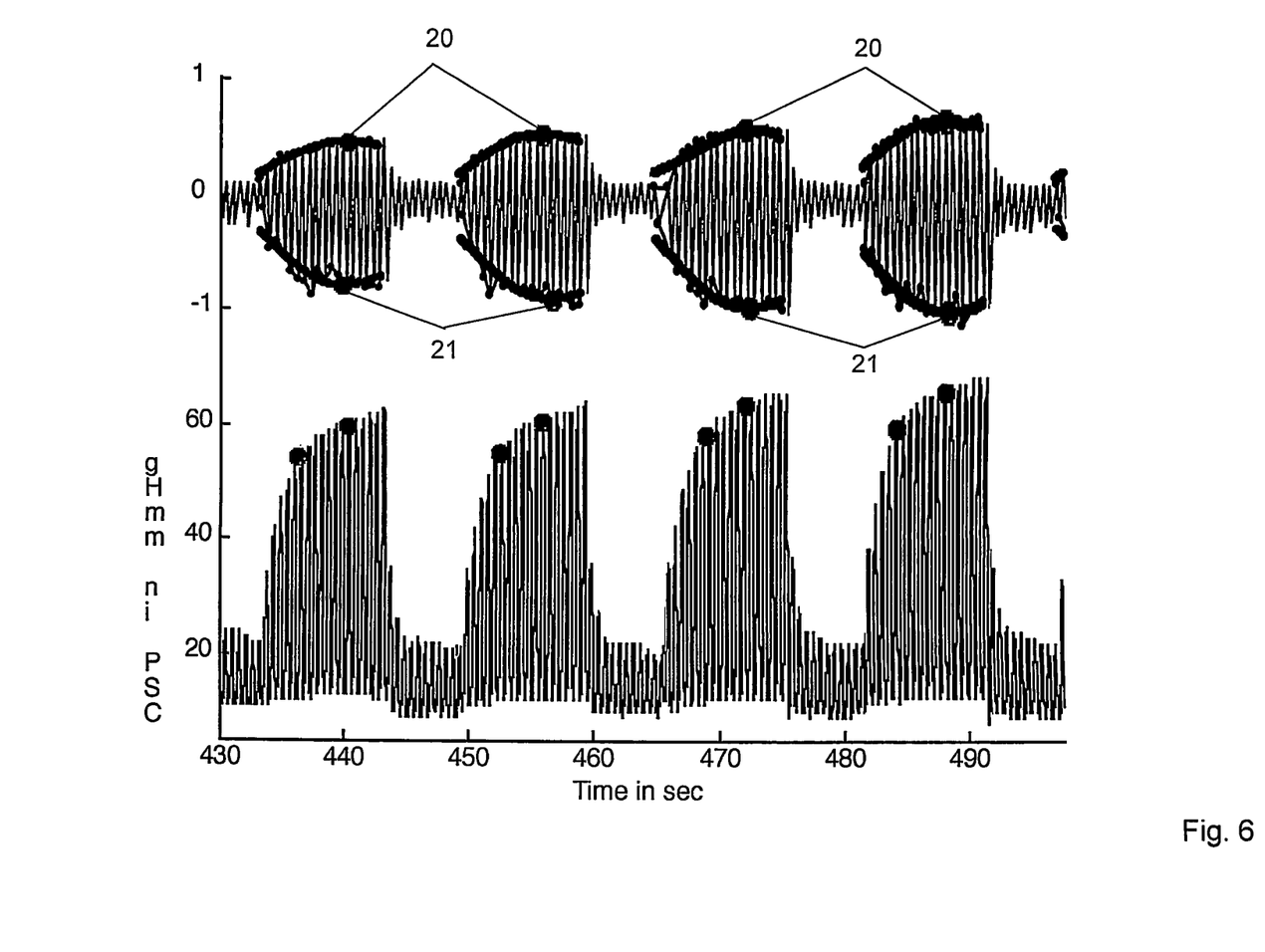
FIG. 6 illustrates the curves according to FIG. 3 and FIG. 4 over a plurality of occlusion and release phases.

FIG. 6 depicts the pressure curve and the respective first derivative dp/dt for a plurality of consecutive occlusion and release phases. The approximated curves 18 and 19 are illustrated too, and the maximum 20 and minimum 21 respectively occurring during the individual occlusion phases are indicated. From the maxima 20 and the minima 21, a series of extreme values can each be formed, which can each be evaluated in terms of the development of a maximum or minimum in order to determine the optimum time for terminating the intermittent occlusion based on the results of this evaluation. A successful progress of the treatment by intermittent occlusion may result in the value of point 20 increasing from one occlusion phase to the next, or at least a trend towards a rise of said value being recognizable over a plurality of occlusion phases. An increase in the value of point 20 allows for conclusions as to a rise of the myocardial contractility. When the value of point 20 reaches a pregiven desired value or a plateau value, the intermittent occlusion, and hence the treatment, can be terminated.

It is, however, more frequently observed during a treatment by intermittent occlusion that the value of point 21 declines. The value of point 21 is representative of the diastolic phase of the relaxation of the heart. The value will be the lower, the higher the left-ventricular pressure drop speed, i.e. the more rapidly the pressure drop in the occluded coronary sinus during the diastole. The determination of the time of termination of the intermittent occlusion, thus, may also be effected as a function of the value of point 21. The intermittent occlusion, and hence the treatment, can, for instance, be terminated as the value of point 21 reaches a pregiven desired value or a plateau value.

Even a combination of the evaluation of the change of the value of point 20 and the change of the value of point 21 can be useful.

Further treatment may again become necessary later on, when the constant monitoring of defined physiological parameters reveals that the heart function has deteriorated, for instance, if a measurement of the electrical impedance or the electrical conductivity of the thorax and, in particular, of the heart and/or lungs indicates a rise in the fluid contents in that area.

The invention claimed is:

1. A device for the intermittent occlusion of a coronary sinus for use in a method for treating heart or circulatory disturbances in a patient, comprising:
    an occlusion device adapted to be activated to provide an intermittent occlusion of a coronary sinus when the occlusion device is positioned in the coronary sinus;
    a control device connected with the occlusion device;
    at least one electrocardiogram (ECG) sensor configured to detect of one or more ECG signals while the occlusion device is positioned in the coronary sinus; and
    a measurement memory fed by the sensor and adapted to store a ECG measurement series, wherein the ECG measurement series is fed to the control device which is configured for computational evaluation of the ECG measurement series so that the control device cooperates with the occlusion device to initiate or terminate the intermittent occlusion as a function of the computational evaluation of the ECG measurement series.

2. A device according to claim 1, further comprising an evaluation circuit configured to evaluate the one or more ECG signals.

3. A device according to claim 1, wherein the control device is configured to effect the computational evaluation after every measurement determination.

4. A device according to claim 1, wherein the control device configured to cooperate with the occlusion device to start a new measurement series at one or more of the initiation and termination of the intermittent occlusion.

5. A device according to claim 1, wherein the control device is configured for the computational evaluation which includes a statistical evaluation by which recognition of a trend is provided and short-term outliers are suppressed.

6. A device according to claim 1, wherein the occlusion device comprises an electrically driven actuator.

7. A device according to claim 1, wherein the device is configured to be an implantable device.

* * * * *